United States Patent
Wells et al.

(10) Patent No.: US 11,481,038 B2
(45) Date of Patent: Oct. 25, 2022

(54) GESTURE RECOGNITION IN CONTROLLING MEDICAL HARDWARE OR SOFTWARE

(71) Applicant: Hologic, Inc., Marlborough, MA (US)

(72) Inventors: Timothy N. Wells, Manchester, CT (US); Shawn St. Pierre, New Milford, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/214,429

(22) Filed: Mar. 26, 2021

(65) Prior Publication Data

US 2021/0303078 A1    Sep. 30, 2021

Related U.S. Application Data

(60) Provisional application No. 63/001,072, filed on Mar. 27, 2020.

(51) Int. Cl.
*G06F 3/01* (2006.01)
(52) U.S. Cl.
CPC .............. *G06F 3/017* (2013.01); *G06F 3/011* (2013.01)
(58) Field of Classification Search
CPC ........... G06F 3/011; G06F 3/017; A61B 34/30
See application file for complete search history.

(56) References Cited

U.S. PATENT DOCUMENTS

| | | | |
|---|---|---|---|
| 4,821,727 A | 4/1989 | Levene et al. | |
| 4,907,156 A | 6/1990 | Doi et al. | |
| 5,078,142 A | 1/1992 | Siczek et al. | |
| 5,129,911 A | 7/1992 | Siczek et al. | |
| 5,133,020 A | 7/1992 | Giger et al. | |
| 5,219,351 A | 6/1993 | Teubner | |
| 5,240,011 A | 8/1993 | Assa | |
| 5,280,427 A | 1/1994 | Magnusson | |

(Continued)

FOREIGN PATENT DOCUMENTS

| | | |
|---|---|---|
| CN | 202161328 | 3/2012 |
| CN | 102429678 | 5/2012 |

(Continued)

OTHER PUBLICATIONS

Han et al., "MatchNet: Unifying Feature and Metric Learning for Patch-Based Matching", 2015 IEEE Conference on Computer Vision and Pattern Recognition (CVPR), Boston, MA, 2015, pp. 3279-3286.

(Continued)

*Primary Examiner* — Mark Edwards
*Assistant Examiner* — Chayce R Bibbee
(74) *Attorney, Agent, or Firm* — Merchant & Gould P.C.

(57) ABSTRACT

Examples of the present disclosure describe systems and methods for using gesture recognition to control medical hardware and software. In aspects, an activation signal may be received by an input processing system, such as a gesture recognition system, a voice recognition system, or a touch-based system. After receiving the activation signal, user input may be received by the input processing system. The user input may be processed to determine a current or applicable context. Based on the context, one or more actions corresponding to the user input may be identified. The input processing system may then cause the identified action(s) to be performed.

20 Claims, 7 Drawing Sheets

(56) References Cited

U.S. PATENT DOCUMENTS

| | | |
|---|---|---|
| 5,289,520 A | 2/1994 | Pellegrino et al. |
| 5,343,390 A | 8/1994 | Doi et al. |
| 5,386,447 A | 1/1995 | Siczek |
| 5,415,169 A | 5/1995 | Siczek et al. |
| 5,426,685 A | 6/1995 | Pellegrino et al. |
| 5,491,627 A | 2/1996 | Zhang et al. |
| 5,594,769 A | 1/1997 | Pellegrino et al. |
| 5,609,152 A | 3/1997 | Pellegrino et al. |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,872,828 A | 2/1999 | Niklason et al. |
| 6,022,325 A | 2/2000 | Siczek et al. |
| 6,101,236 A | 8/2000 | Wang et al. |
| 6,102,866 A | 8/2000 | Nields et al. |
| 6,245,028 B1 | 6/2001 | Furst et al. |
| 6,293,282 B1 | 9/2001 | Lemelson |
| 6,459,925 B1 | 10/2002 | Nields et al. |
| 6,468,226 B1 | 10/2002 | McIntyre, IV |
| 6,480,565 B1 | 11/2002 | Ning |
| 6,620,111 B2 | 9/2003 | Stephens et al. |
| 6,626,849 B2 | 9/2003 | Huitema et al. |
| 6,638,235 B2 | 10/2003 | Miller et al. |
| 6,683,934 B1 | 1/2004 | Zhao |
| 6,758,824 B1 | 7/2004 | Miller et al. |
| 6,987,331 B2 | 1/2006 | Koeppe |
| 7,123,684 B2 | 10/2006 | Jing et al. |
| 7,245,694 B2 | 7/2007 | Jing et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,634,050 B2 | 12/2009 | Muller et al. |
| 7,697,660 B2 | 4/2010 | Ning |
| 7,702,142 B2 | 4/2010 | Ren et al. |
| 7,760,924 B2 | 7/2010 | Ruth et al. |
| 7,787,936 B2 | 8/2010 | Kressy |
| 7,831,296 B2 | 11/2010 | DeFreitas et al. |
| 7,869,563 B2 | 1/2011 | DeFreitas |
| 7,991,106 B2 | 8/2011 | Ren et al. |
| 8,532,745 B2 | 9/2013 | DeFreitas et al. |
| 8,594,274 B2 | 11/2013 | Hoernig et al. |
| 9,020,579 B2 | 4/2015 | Smith |
| 9,901,309 B2 | 2/2018 | DeFreitas et al. |
| 10,092,358 B2 | 10/2018 | DeFreitas |
| 10,335,094 B2 | 7/2019 | DeFreitas |
| 10,357,211 B2 | 7/2019 | Smith |
| 10,456,213 B2 | 10/2019 | DeFreitas |
| 10,595,954 B2 | 3/2020 | DeFreitas |
| 2001/0038681 A1 | 11/2001 | Stanton et al. |
| 2002/0113681 A1 | 8/2002 | Byram |
| 2002/0122533 A1 | 9/2002 | Marie et al. |
| 2003/0018272 A1 | 1/2003 | Treado et al. |
| 2003/0073895 A1 | 4/2003 | Nields et al. |
| 2003/0135115 A1 | 7/2003 | Burdette et al. |
| 2004/0077938 A1 | 4/2004 | Mark et al. |
| 2004/0081273 A1 | 4/2004 | Ning |
| 2004/0127789 A1 | 7/2004 | Ogawa |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0049497 A1 | 3/2005 | Krishnan et al. |
| 2005/0049521 A1 | 3/2005 | Miller et al. |
| 2005/0084060 A1 | 4/2005 | Seppi et al. |
| 2005/0089205 A1 | 4/2005 | Kapur |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2006/0009693 A1 | 1/2006 | Hanover et al. |
| 2006/0025680 A1 | 2/2006 | Jeune-Iomme |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0257009 A1 | 11/2006 | Wang |
| 2006/0269040 A1 | 11/2006 | Mertelmeier |
| 2007/0019846 A1 | 1/2007 | Bullitt et al. |
| 2007/0114424 A1 | 5/2007 | Danielsson et al. |
| 2007/0225600 A1 | 9/2007 | Weibrecht et al. |
| 2007/0263765 A1 | 11/2007 | Wu |
| 2008/0019581 A1 | 1/2008 | Gkanatsios et al. |
| 2008/0045833 A1 | 2/2008 | DeFreitas et al. |
| 2008/0101537 A1 | 5/2008 | Sendai |
| 2008/0152086 A1 | 6/2008 | Hall |
| 2008/0187095 A1 | 8/2008 | Boone et al. |
| 2008/0198966 A1 | 8/2008 | Hjarn |
| 2009/0003519 A1 | 1/2009 | DeFreitas |
| 2009/0080604 A1 | 3/2009 | Shores et al. |
| 2009/0143674 A1 | 6/2009 | Nields |
| 2009/0171244 A1 | 7/2009 | Ning |
| 2009/0177495 A1 | 7/2009 | Abousy et al. |
| 2009/0296882 A1 | 12/2009 | Gkanatsios et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1 | 6/2010 | Navab |
| 2010/0208037 A1 | 8/2010 | Sendai |
| 2011/0019891 A1 | 1/2011 | Puong |
| 2011/0069808 A1 | 3/2011 | Defreitas et al. |
| 2011/0087132 A1 | 4/2011 | DeFreitas et al. |
| 2011/0110576 A1 | 5/2011 | Kreeger |
| 2011/0182402 A1 | 7/2011 | Partain |
| 2011/0237927 A1 | 9/2011 | Brooks et al. |
| 2012/0014504 A1 | 1/2012 | Jang |
| 2012/0134464 A1 | 5/2012 | Hoernig et al. |
| 2012/0238870 A1 | 9/2012 | Smith et al. |
| 2013/0022165 A1 | 1/2013 | Jang |
| 2013/0044861 A1 | 2/2013 | Muller |
| 2013/0108138 A1 | 5/2013 | Nakayama |
| 2013/0259193 A1 | 10/2013 | Packard |
| 2014/0064444 A1 | 3/2014 | Oh |
| 2014/0073913 A1 | 3/2014 | DeFreitas et al. |
| 2015/0347693 A1 | 12/2015 | Lam et al. |
| 2015/0375399 A1* | 12/2015 | Chiu ............... B25J 9/1612 345/156 |
| 2016/0000399 A1 | 1/2016 | Halmann et al. |
| 2016/0022364 A1 | 1/2016 | DeFreitas et al. |
| 2016/0216769 A1* | 7/2016 | Goetz ............... G06F 3/017 |
| 2016/0235380 A1 | 8/2016 | Smith |
| 2018/0068066 A1 | 3/2018 | Bronkalla |
| 2018/0256118 A1 | 9/2018 | DeFreitas |
| 2019/0015173 A1 | 1/2019 | DeFreitas |
| 2019/0064929 A1* | 2/2019 | Tomeh ............... H04L 12/2803 |
| 2019/0138693 A1 | 5/2019 | Muller et al. |
| 2019/0188848 A1 | 6/2019 | Madani et al. |
| 2019/0221304 A1 | 7/2019 | Ionasec |
| 2019/0290221 A1 | 9/2019 | Smith |
| 2019/0295248 A1 | 9/2019 | Nakamura et al. |
| 2020/0043600 A1 | 2/2020 | Glottmann et al. |
| 2020/0046303 A1 | 2/2020 | DeFreitas |
| 2020/0093562 A1 | 3/2020 | DeFreitas |
| 2020/0167920 A1 | 5/2020 | Hall et al. |
| 2020/0205928 A1 | 7/2020 | DeFreitas |
| 2020/0286613 A1 | 9/2020 | Rego |
| 2020/0390404 A1 | 12/2020 | DeFreitas |
| 2021/0000553 A1 | 1/2021 | St. Pierre |
| 2021/0030366 A1 | 2/2021 | Chen |
| 2021/0035680 A1 | 2/2021 | Chen |
| 2021/0098120 A1 | 4/2021 | Kshirsagar |
| 2021/0100626 A1 | 4/2021 | St. Pierre |

FOREIGN PATENT DOCUMENTS

| | | |
|---|---|---|
| CN | 108492874 | 9/2018 |
| DE | 102011087127 | 5/2013 |
| EP | 1428473 | 6/2004 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2003-531516 | 10/2003 |

(56) References Cited

FOREIGN PATENT DOCUMENTS

| | | |
|---|---|---|
| JP | 2006-519634 | 8/2006 |
| JP | 2007-130487 | 5/2007 |
| JP | 2009-522005 | 6/2009 |
| JP | 2009-526618 | 7/2009 |
| JP | 2010-137004 | 6/2010 |
| JP | 2012-501750 | 1/2012 |
| JP | 2014-507250 | 3/2014 |
| JP | 2015-506794 | 3/2015 |
| WO | 93/17620 | 9/1993 |
| WO | 94/06352 | 3/1994 |
| WO | 1997/00649 | 1/1997 |
| WO | 00/51484 | 9/2000 |
| WO | 2005/079306 | 9/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008/054436 | 5/2008 |
| WO | 2009/026587 | 2/2009 |
| WO | 2010/028208 | 3/2010 |
| WO | 2011/043838 | 4/2011 |
| WO | 2012/001572 | 1/2012 |
| WO | 2012/068373 | 5/2012 |
| WO | 2012/112627 | 8/2012 |
| WO | 2012/122399 | 9/2012 |
| WO | 2013/001439 | 1/2013 |
| WO | 2013/078476 | 5/2013 |
| WO | 2013/123091 | 8/2013 |
| WO | 2015/061582 | 4/2015 |
| WO | 2016/103094 | 6/2016 |
| WO | 2016/184746 | 11/2016 |
| WO | 2019/030410 | 2/2019 |
| WO | 2016/057960 | 5/2019 |
| WO | 2019/091807 | 5/2019 |
| WO | 2019/227042 | 11/2019 |
| WO | 2021/195370 | 9/2021 |

OTHER PUBLICATIONS

Choi Bareum et al., "Surgical-tools detection based on Convolutional Neural Network in laparoscopic robot-assisted surgery", 2017 39th Annual International Conference of the IEEE Engineering in Medicine and Biology Society (EMBC), IEEE, Jul. 11, 2017, pp. 1756-1759.
"Filtered Back Projection", (NYGREN), published May 8, 2007, URL: http://web.archive.org/web/19991010131715/http://www.owlnet.rice.edu/~elec539/Projects97/cult/node2.html, 2 pgs.
"Supersonic to feature Aixplorer Ultimate at ECR", AuntiMinnie.com, 3 pages (Feb. 2018).
Berg, WA et al., "Combined screening with ultrasound and mammography vs mammography alone in women at elevated risk of breast cancer", JAMA 299:2151-2163, 2008.
Burbank, Fred, "Stereotactic Breast Biopsy: Its History, Its Present, and Its Future", published in 1996 at the Southeastern Surgical Congress, 24 pages.
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Carton, AK, et al., "Dual-energy contrast-enhanced digital breast tomosynthesis—a feasibility study", BR J Radiol. Apr. 2010;83 (988):344-50.
Chen, SC, et al., "Initial clinical experience with contrast-enhanced digital breast tomosynthesis", Acad Radio. Feb. 2007 14(2):229-38.
Diekmann, F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Dromain, Clarisse et al., "Dual-energy contrast-enhanced digital mammography: initial clinical results", European Radiology, Sep. 14, 2010, vol. 21, pp. 565-574.
E. Shaw de Paredes et al., "Interventional Breast Procedure", published Sep./Oct. 1998 in Curr Probl Diagn Radiol, pp. 138-184.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Freiherr, G., "Breast tomosynthesis trials show promise", Diagnostic Imaging—San Francisco 2005, V27; N4:42-48.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Giger et al. "Development of a smart workstation for use in mammography", in Proceedings of SPIE, vol. 1445 (1991), p. 101103; 4 pages.
Giger et al., "An Intelligent Workstation for Computer-aided Diagnosis", in RadioGraphics, May 1993, 13:3 pp. 647-656; 10 pages.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Jochelson, M., et al, "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, et. al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin,JM, et al., Dual-energy contrast-enhanced digital subtraction mammography: feasibility. Radiology 2003; 229:261-268.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Poplack, SP, et al, Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Shrading, Simone et al., "Digital Breast Tomosynthesis-guided Vacuum-assisted Breast Biopsy: Initial Experiences and Comparison with Prone Stereotactic Vacuum-assisted Biopsy", the Depart- (56) References Cited

OTHER PUBLICATIONS ment of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", AM J Clin Pathol. Nov. 2004 122(5):696-703.
Yuan, Yading et al., "Correlative feature analysis on FFDM", Medical Physics, vol. 35, No. 12, Nov. 13, 2008, pp. 5492-5494.

\* cited by examiner

GESTURE RECOGNITION IN CONTROLLING MEDICAL HARDWARE OR SOFTWARE

CROSS-REFERENCE TO RELATED APPLICATIONS

This application claims the benefit of U.S. Provisional Application No. 63/001,072 filed on Mar. 27, 2020, the disclosure of which is hereby incorporated by reference herein in its entirety.

BACKGROUND

Many healthcare professionals routinely engage in various tasks that require repetitive movements. In many cases, these tasks cause the healthcare professionals to incur injuries from poor posture or excessive load manipulation due to device location, patient position, or other environmental factors. Additionally, several tasks require interaction with potentially unsterile devices while the healthcare professionals are in sterile environments. As a consequence, the risk of infection may be unnecessarily increased for patients while the tasks are being performed It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for using gesture recognition to control medical hardware and software. In aspects, an activation signal may be received by an input processing system, such as a gesture recognition system, a voice recognition system, or a touch-based system. After receiving the activation signal, user input may be received by the input processing system. The user input may be processed to determine a current or applicable context. Based on the context, one or more actions corresponding to the user input may be identified. The input processing system may then cause the identified action(s) to be performed.

Aspects of the present disclosure provide a system comprising: at least one processor; and memory coupled to the at least one processor, the memory comprising computer executable instructions that, when executed by the at least one processor, performs a method comprising: collecting sensor data associated with gesture input, wherein the gesture input corresponds to a user interaction with one or more medical components; determining an input context for the gesture input using the sensor data, wherein the determining comprises applying the sensor data to one or more gesture recognition algorithms; correlating the gesture input to one or more actions, wherein the one or more actions correspond to a set of commands for interacting with the one or more medical components; and causing automated performance of the one or more actions by the one or more medical components.

Aspects of the present disclosure further provide a method comprising: detecting, by an input processing system, a gesture from a user, wherein the gesture is intended to manipulate one or more medical components, and wherein the user does not make physical contact with the one or more medical components during the gesture; collecting, by a gesture detection sensor of the input processing system, sensor data associated with the gesture; applying the sensor data to a gesture recognition algorithm to determine an input context for the gesture; based on the input context, correlating the gesture with one or more actions, wherein the one or more actions represent a manipulation of the one or more medical components; and causing, by an input processing system, the one or more medical components to automatically perform of the one or more actions.

Aspects of the present disclosure further provide a computer-readable media storing computer executable instructions that when executed cause a computing system to perform a method comprising: receiving an input; determining the input is an activation signal; based on the activation signal, activating an input detection mode; detecting, by the activated input detection mode, a gesture; collecting sensor data associated with gesture, wherein the gesture corresponds to a user interaction with one or more medical components; applying the sensor data to one or more gesture recognition algorithms to determine an input context for the gesture; based on the input context, correlating the gesture with one or more actions, wherein the one or more actions represent a manipulation of the one or more medical components; and causing the one or more medical components to automatically perform of the one or more actions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Many healthcare professionals are required to perform the same (or similar) tasks or set of tasks routinely. Often, these tasks require a specific set of physical movements or actions to be performed to accomplish the task. Over time, the repeated performance of these physical movements or actions may cause the healthcare professionals performing the tasks to incur injuries or discomfort. As one example, healthcare professionals may incur repetitive stress injuries due to poor posture or excessive load manipulation while controlling a medical device or software for an extended time period. These injuries are often exacerbated by inconvenient or awkward medical device location, patient positioning, or other environmental factors. Additionally, in many instances, the tasks require the healthcare professionals to interact with objects that may be unsterile or may be outside a sterile field. For instance, during a surgical procedure, a healthcare professional operating in sterile field may need to physically interact with a computing device comprising medical software. The computing device may be outside the sterile field. As a result, each physical interaction with the computing device represents a scenario in which contaminates may be introduced into the procedure.

To address such issues with many healthcare professional tasks, the present disclosure describe systems and methods for using gesture recognition to control medical devices and software. In aspects, an input processing system may be accessible to one or more healthcare professionals. The input processing system may comprise or have access to various hardware components and/or software components. For example, the input processing system may comprise one or more sensors, such as gesture detection sensor, acoustic sensors, and touch-based sensors. One or more of the sensors may be associated with an input recognition system, such as a gesture recognition system, a voice recognition system, a touch-based system, etc. For example, an acoustic sensor may be integrated in to a natural language understanding (NLU) system configured to interpret utterances (and other sounds) received from one or more sources (e.g., users, software components, etc.).

In aspects, the input processing system may receive an activation signal from a source. The activation signal may be detected by one or more sensors of the input processing system. In response to receiving the activation signal, the input processing system may activate one or more input detection modes, systems, or applications. Example input detection modes may include gesture recognition mode, voice recognition mode, touch recognition mode, etc. Once activated, the input detection mode(s) may receive user input from one or more users. Examples of user input include gestures, speech (or other sounds), touch input, textual input, etc. Upon receiving the user input, the input processing system may process the user input to determine an input context. An input context, as used herein, may relate to (or otherwise indicate) an input detection mode, an application/service entry point (e.g., an application/service used to provide, or associated with, the input), a hardware component or device, user settings or preferences, or other user related information. Based on the determined input context, the input processing system may identify one or more actions or events corresponding to the user input. In examples, the actions/events may represent a set of commands or instructions for performing at least a portion of one or more tasks. The input processing system may then cause at least a subset of the identified actions/events to be performed using hardware and/or software components accessible to the input processing system.

Accordingly, the present disclosure provides a plurality of technical benefits including but not limited to: using gestures and/or voice commands to control medical hardware and software, implementing gesture-based and/or voice-based instructions or commands into existing medical devices, determining current user/device context, mapping received user input to predefined actions/events, performing actions/events based on user and/or device context, reducing the occurrence of healthcare professional injuries, and decreasing the likelihood of introducing contaminates during medical procedures or exams, among others.

Figure 1:
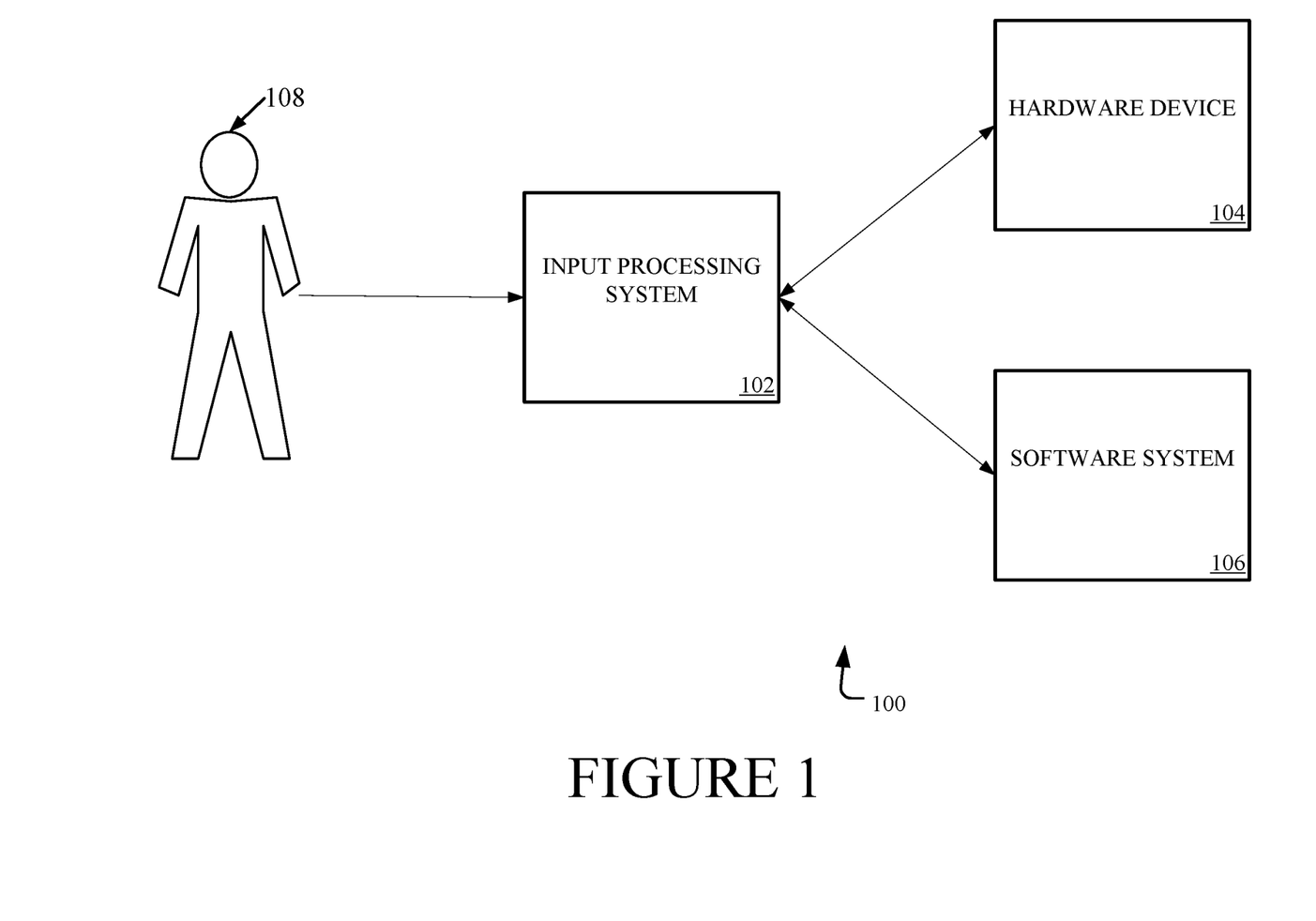
FIG. 1 illustrates an overview of an example system for using gesture recognition to control medical hardware and software, as described herein.

FIG. 1 illustrates an overview of an example system for using gesture recognition to control medical devices and software as described herein. Example system 100 as presented is a combination of interdependent components that interact to form an integrated system for using gesture recognition to control medical devices and software. Components of the system may be hardware components (e.g., used to execute/run operating system (OS)) or software components (e.g., applications, application programming interfaces (APIs), modules, virtual machines, runtime libraries, etc.) implemented on, and/or executed by, hardware components of the system. In one example, example system 100 may provide an environment for software components to run, obey constraints set for operating, and utilize resources or facilities of the system 100. For instance, software may be run on a processing device such as a personal computer (PC), mobile device (e.g., smart device, mobile phone, tablet, laptop, personal digital assistant (PDA), etc.), and/or any other electronic devices. In other examples, the components of systems disclosed herein may be distributed across multiple devices. For instance, input may be entered on a first computing device and information may be processed or accessed using one or more additional computing devices.

As one example, the system 100 may comprise input processing system 102, hardware device 104, and software system 106. One of skill in the art will appreciate that the scale of systems such as system 100 may vary and may include more or fewer components than those described in FIG. 1. For instance, in some examples, the functionality and components of hardware device 104 and software system 106 may be integrated into a single hardware device or computing system. Alternately, the functionality and components of input processing system 102 may be distributed across multiple hardware devices or computing systems.

Input processing system 102 may be configured to collect sensor data. In aspects, input processing system 102 may comprise one or more sensor components. Each of the sensor components may be configured to detect and/or record data from one or more input sources. For example, an input source, such as user 108, may provide a speech-based activation command to input processing system 102. The activation command may be detected by an acoustic sensor of input processing system 102. As another example, the input provider may provide a gesture-based command to input processing system 102. The activation command may be detected by one or more cameras and/or motion detectors of input processing system 102. In some examples, input processing system 102 may evaluate the detected sensor data to determine whether the sensor data corresponds to a recognized command or instruction. For instance, an acoustic sensor may provide detected speech data to an NLU system accessible to input processing system 102. The NLU system may process the speech data to determine whether the speech data corresponds to, for example, an activation signal.

Input processing system 102 may be further configured to control one or more input detection modes. In aspects, input processing system 102 may process collected sensor data by categorizing the sensor data into one or more input categories. For example, the sensor data may categorized as a gesture, speech, or touch-based data. Processing the sensor data may further or alternately comprise determining an input context for the sensor data. The input context may identity an application or device actively associated with input processing system 102, or one or more user settings or preferences. For example, the input context may identify an application currently being used by a user. Based on a determined input category and/or an input context, input processing system 102 may activate one or more input detection modes, such as a gesture recognition mode, a voice recognition mode, or a touch recognition mode. Alternately, the input detection modes may be in an always-on state such that the input detection modes are ready to detect input without requiring an activation signal or wake signal.

In aspects, input processing system 102 may use the selected input detection mode to process the sensor data. The processing comprise evaluating one or more images or videos in the sensor data to detect a gesture, a posture, a body part, a body part orientation, a configuration of features, or the like. Processing the sensor data may additionally comprise evaluating received audio data to detect one or more words or phrases. After processing the sensor data, the selected input detection mode may be used to compare the processed sensor data to a list or mapping of actions or events. Each action or event may represent a set of commands or instructions for performing at least a portion of one or more tasks. Based on the comparison, input processing system 102 one or more of the actions/events indicated by the sensor data. For example, input processing system 102 may process a set of images corresponding to a received gesture using a gesture recognition mode. The set of images may be compared against a data store of stored images. The comparison may indicate that the set of images correlates to a specific action or function associated with a medical device. Accordingly, the specific action or function may be selected by the gesture recognition mode.

Input processing system 102 may further be configured to cause one or more actions to be performed. In aspects, input processing system 102 may be configured to communicate with hardware device 104 and/or software system 106 via a network or direct connection. Examples of hardware device 104 include medical imaging devices (e.g., ultrasound devices, x-ray device, magnetic resonance imaging (MRI) devices, etc.) or components thereof (e.g., gantry, x-ray tube, camera units, compression paddles, patient table/bed, etc.). Examples of software system 106 include electronic medical record (EMR) applications, medical image review software, medical imaging software, annotation utilities, workflow/task management utilities, etc. In some aspects, input processing system 102 may provide a selected action/function to hardware device 104 and/or software system 106. Upon receiving the selected action/function, hardware device 104 and/or software system 106 may perform an action or event indicated by the selected action/function. For example, in response to receiving a gesture-based instruction, input processing system 102 may provide a gantry movement instruction to an x-ray device in communication with input processing system 102.

Figure 2:
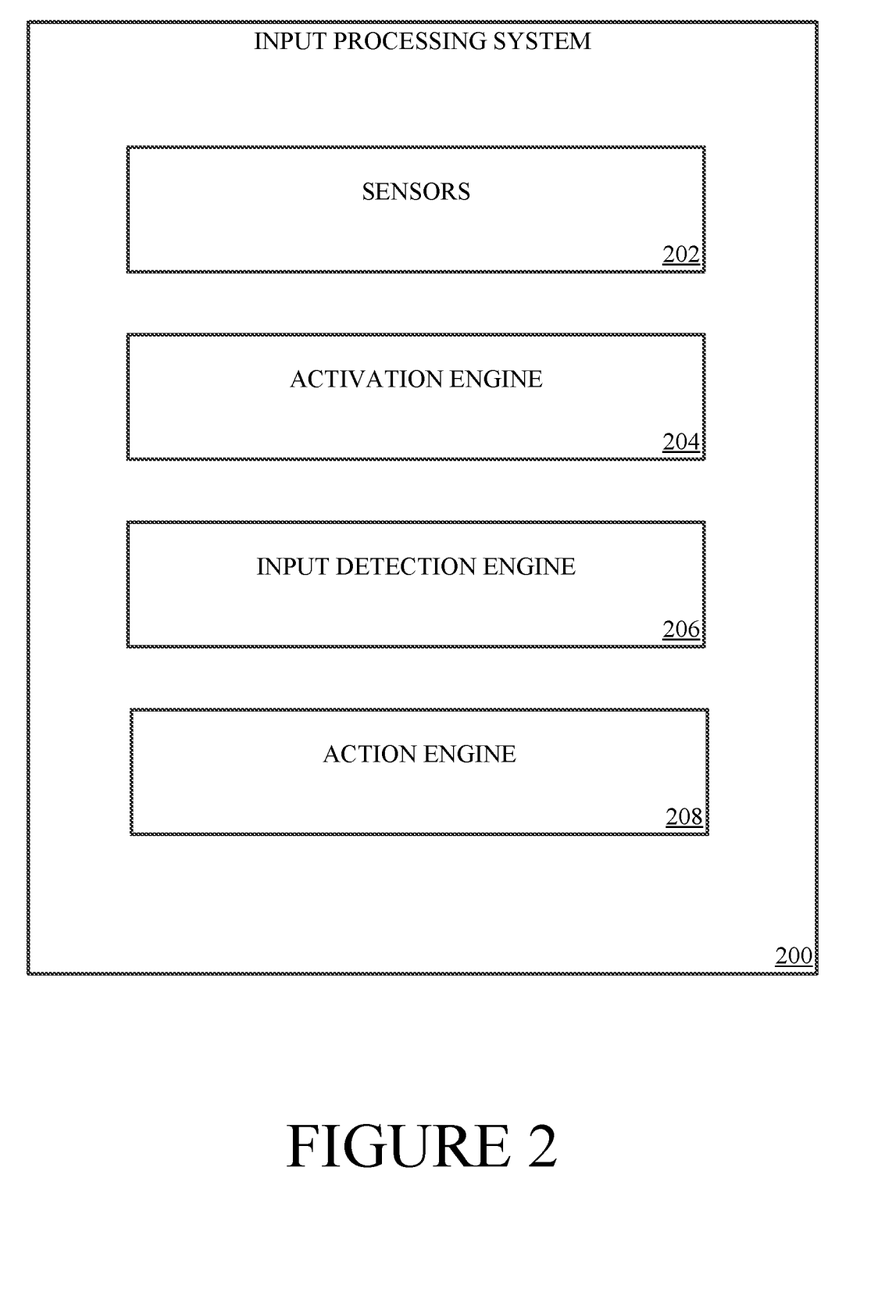
FIG. 2 is a diagram of an example input processing system for using gesture recognition to control medical hardware and software, as described herein.

FIG. 2 illustrates an overview of an exemplary input processing system 200 for using gesture recognition to control medical devices and software. In examples, input processing system 200 may be implemented into, or interface with, one or more devices or systems, such as medical devices and software. Input processing system 200 may be implemented as a standalone system or application, an add-on to an existing system/application, or some combination thereof. For example, input processing system 200 may primarily (or exclusively) utilize components (e.g., sensors, user interfaces, etc.) of input processing system 200, integrate such components into existing systems/applications, or utilize such components of existing systems/applications. In FIG. 2, input processing device 200 comprises sensor(s) 202, activation engine 204, input recognition engine 206, and action engine 208. One of skill in the art will appreciate that input processing system 200 may include more or fewer components than those described in FIG. 2.

Sensor(s) 202 may be configured to detect and/or collect input signals. In aspects, sensor(s) 202 may receive input signals from one or more input sources, such as users, hardware components, or software components. For example, sensor(s) 202 may detect a gesture or speech provided by a healthcare professional. As another example, sensor(s) 202 may detect the presence of a particular hardware component, such as an ultrasound probe, a compression paddle, a gantry component, etc. As yet another example, sensor(s) 202 may detect a state change indication (e.g., a power on, resume, or initiate function signal) from a software component communication with input processing system 200. Example sensors include, but are not limited to, imaging sensors, light sensors, radar sensors, acoustic sensors, touchscreen sensors, proximity sensors, inertial sensors, accelerometers, ambient temperature sensors, gyroscopic sensors, magnetometers, GPS sensors, Wi-Fi sensors, etc. The detected sensor data may be stored in one or more storage locations.

Activation engine 204 may be configured to activate a mode of input detection. In aspects, sensor data collected by sensor(s) 202 may be provided to activation engine 204. Activation engine 204 may process the sensor data using one or more input classification techniques. For example, activation engine 204 may categorize the sensor data according to the type of sensor that collected the sensor data (e.g., sensor data collected by a gesture detection sensor is categorized as gesture data). Alternately, activation engine 204 may evaluate the sensor data using a machine learning (ML) classification model or equation. For example, activation engine 204 may provide speech-based sensor data to a natural language understanding (NLU) system configured to interpret utterances (and other sounds) received from one or more sources. Based on the processed sensor data, activation engine 204 may determine whether the sensor data corresponds to a recognized activation request. The determination may comprise comparing the sensor data to a list of known "wake" gestures or words. A wake gesture or word, as used herein, may refer to a command or occurrence that activates one or more functions or interfaces of a device. If the sensor data is determined to correspond to a wake gesture or word, activation engine 204 may provide an activation request to an input detection/recognition component, such as input recognition engine 206. The activation request may include the type or category of the received sensor data.

Input recognition engine 206 may be configured to activate one or more input modes. In aspects, input recognition engine 206 may receive an activation request from, for example, activation engine 204. The activation request may cause input recognition engine 206 to activate one or more sensor functions/components, or to enable the receipt of sensor data from sensors(s) 202. After the activating the appropriate sensor functionality, user input may be detected by the sensor functions/components of input recognition engine 206 and/or sensor(s) 202. The user input may be provided to input recognition engine 206 for processing. Processing the user input may comprise categorizing the user input into one or more input categories. For example, input recognition engine 206 may use one or more ML techniques to determine whether the user input is a gesture, speech, or touch-based data. Processing the user input may further or alternately comprise determining an input context for the user input. The input context may identity or relate to an application, service, or device associated with the user input. For example, the input context may identify the application that is active on a particular device or system when the user input was received. Based on the processed user input, input recognition engine 206 may select and/or activate one or more input recognition modes, such as a gesture recognition mode, a voice recognition mode, or a touch recognition mode. In some examples, each input recognition mode may correspond to an input recognition engine type. For example, a gesture input recognition mode may use a gesture recognition engine. In other examples, multiple input recognition modes may use the same input recognition engine.

In aspects, input recognition engine 206 may provide the user input (and/or the corresponding processed user input data) to the selected input recognition mode. The input detection mode may process the user input to identify a corresponding command or instruction. Processing the sensor data may comprise using one or more gesture recognition algorithms to evaluate one or more images or videos to detect a gesture, a posture, a body part, a body part orientation, a configuration of features, or the like. Example gesture recognition algorithms include 3D model-based algorithms, skeletal-based algorithms, and appearance-based algorithms and models. Processing the sensor data may additionally comprise evaluating received audio data to detect one or more words or phrases. After processing the user input, the selected input detection mode may compare the processed user input to one or more stored image or model templates. The stored templates may be organized according to user input type and/or input context. For example, the stored templates associated with gesture commands for manipulating a hardware device may be stored in a first file or location, and the stored templates associated with gesture commands for manipulating a software application may be stored in a second file or location. In examples, the stored templates may comprise images representing various body parts in various configurations and/or orientations. The stored templates may also comprise a set of commands or instructions corresponding to the images. Based on the comparison of the processed user input to the stored templates, input recognition engine 206 may select a set of commands or instructions.

Action engine 208 may be configured to execute a selected set of commands or instructions. In aspects, action engine 208 may have access to a set of commands or instructions selected by input recognition engine 206. Action engine 208 may execute the set of commands or instructions to cause a corresponding action or event to occur. For example, input processing system 200 may be integrated with a device such that executing a selected command/instruction causes the device to be manipulated in a manner indicated by the command/instruction. Alternately, action engine 208 may transmit the command/instruction, or an indication of the command/instruction, to a separate device or software system. The separate device or software system may then interpret the transmitted command/instruction such that a local version of the command/instruction is executed by the device or software.

Figure 3:
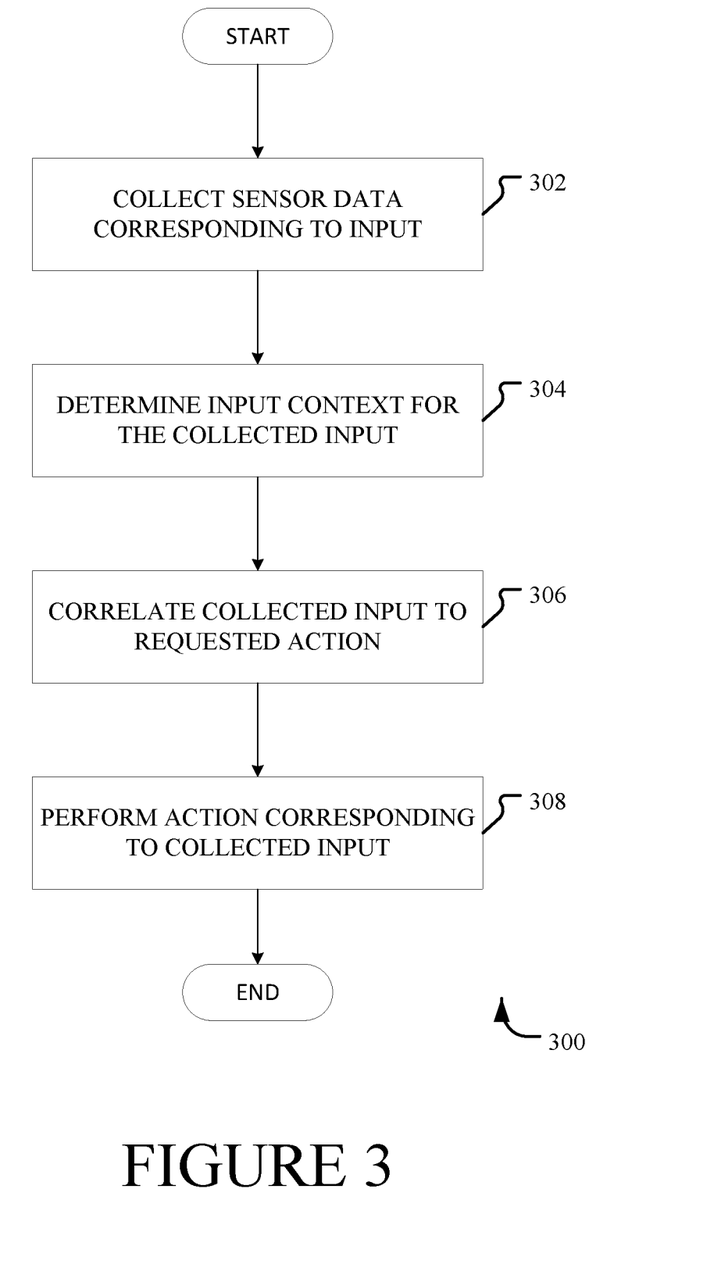
FIG. 3 illustrates an example method for using gesture recognition to control medical hardware and software, as described herein.

Having described various systems that may be employed by the aspects disclosed herein, this disclosure will now describe one or more methods that may be performed by various aspects of the disclosure. In aspects, method 300 may be executed by an example system 100 of FIG. 1 or input processing system 200 of FIG. 2. In such aspects, method 300 may be executed on a device comprising at least one processor configured to store and execute operations, programs, or instructions. However, method 300 is not limited to such examples. In other examples, method 300 may be performed by an application or service for using gesture recognition to control medical devices and software. In at least one example, method 300 may be executed (e.g., computer-implemented operations) by one or more components of a distributed network, such as a web service/distributed network service (e.g., cloud service).

FIG. 3 illustrates an example method 300 for using gesture recognition to control medical devices and software. The gesture recognition described in example method 300 may be implemented by an input processing system, such as example system 100 or input processing system 200. In some examples, the input processing system may provide (or be associated with) a 2D or 3D environment comprising one or more virtualized objects, such as a virtual reality (VR) environment, an augmented reality (AR) environment, or a mixed reality (MR) environment. In such examples, the input processing system may comprise a head-mounted display (HMD) for presenting an environment comprising two dimensional (2D) and/or three dimensional (3D) content to a user. Gestures detected by the input processing system may enable manipulation of the content presented in the HMD environment and/or manipulation of real world objects in communication with the input processing system.

Example method 300 begins at operation 302, where input may be collected from one or more input sources. In aspects, one or more sensor components, such as sensor(s) 202, may be associated with an input processing system. The sensor components may collect data (e.g., sensor data) corresponding to input from one or more input sources. As one example, the sensor components may collect image data corresponding to a user's hand gesture. The image data may comprise several images of the user's hand in various orientations and/or configurations during the hand gesture. As another example, the sensor components may collect speech data corresponding to a user utterance. The speech data may comprise several speech frames that collectively form the user utterance. As yet another example, the sensor components may collect inertial data corresponding user movement within an environment. The inertial data my comprise force and positional data that may be used to present objects in a virtual (or partly virtual) environment.

At operation 304, an input context may be determined for the collected input. In aspects, the sensor data corresponding to the collected input may be provided to an input processing component, such as input recognition engine 206. The input processing component may categorize the collected input into one or more input categories using one or more categorization techniques. For example, input collected using a gesture detection sensor may be categorized as gesture input, whereas input collected using an acoustic sensor may be categorized as speech input. Alternately, collected input may be evaluated by applying the sensor data to one or more input algorithms or models. For example, sensor data may be applied to a gesture recognition model and a speech recognition model. The recognition models may each provide an indication of whether the sensor data is recognizable and/or compatible with the recognition model. Based on an indication from one or more of the recognition models, the collected input may be categorized accordingly.

In aspects, the input processing component may also or alternately determine an input context for the collected input. The input context may be based on an active software component, an identified hardware component, user related information, or some combination thereof. As one example, a mammography image review software application may be determined to be the application that was active (e.g., in focus) at the time the input was collected. Accordingly, the input context may be set to the software application, mammography image review, or a similar context. As another example, a technologist may be manipulating an aspect of an imaging device gantry proximate to the time the input was collected. Accordingly, the input context may be set to gantry motion control or a similar context. As yet another example, a healthcare professional may be interacting with a virtual object within a virtualized environment (e.g., a VR, AR, or MR environment). Accordingly, the input context may be set to the virtual environment or the virtual object. As still yet another example, a particular user may be identified as providing the collected input. The user may be associated with a user profile or a specific set of user privileges indicating hardware or software components accessible to the user. Accordingly, the input context may be set to one or more of the hardware or software components indicated by the user profile/privileges.

At operation 306, collected input may be correlated to one or more actions. In aspects, a set of input data (e.g., sensor data, input category, and/or input context) may be evaluated to determine one or more corresponding actions or events. The evaluation may include the use of one or more gesture and/or image recognition algorithms or models, such as 3D model-based algorithms, skeletal-based algorithms, and appearance-based algorithms and models. In some aspects, the gesture and/or image recognition algorithms or models may be used to compare features of the set of input data to features of stored images or videos. For example, a set of gesture commands may be stored for one or more software and/or hardware components configured to be operable with the gesture recognition techniques described herein. Each gesture command may be associated with a sequence of hand motions that may form the gesture command. Each gesture command may also be associated with a corresponding action. Images in a set of input data for a received gesture may be compared to the stored sequence of hand motions. A gesture command for which the stored sequence of hand motions most closely matches the images in the set of input data may be identified. The action corresponding to the gesture command may then be identified and/or selected.

In some aspects, the gesture and/or image recognition algorithms or models may be used to correlate gesture input to a specific software or hardware component. For example, a user may interact with medical image review software executing in a virtualized environment. Based on the interaction with the medical image review software, gesture and/or movement input may be detected. The detected input may be assigned an input category of "Gesture/Movement" and an input context of "Virtual Environment—Image Review Software." The gesture/movement input data may be provided to a 3D modelling algorithm. Based on the input context, the 3D modelling algorithm may associate the gesture/movement input with the medical image review software. The gesture/movement input may then be applied to one or more actions associated with the medical image review software (e.g., annotating an image, selecting a next/previous image, enlarging/shrinking content, manipulating 3D aspects of image review content, etc.). For instance, the gesture/movement input may be correlated to a set of commands for interacting with the medical image review software. In this example, the gesture input may represent a first set of commands in the medical image review software and a different set of commands in the virtualized environment (e.g., when in the virtualized environment, but not using the medical image review software).

At operation 308, one or more actions corresponding to the collected input may be performed. In aspects, a selected action may be provided to an action execution component, such as action engine 208. The action execution component may execute a set of commands or instructions corresponding to the selected action. For example, collected gesture input may correspond to an action that controls the motion of an imaging device gantry. Upon determining the action corresponding to the gesture input, the action execution component may execute an instruction causing movement of the gantry. Alternately, the action execution component may transmit a command or instruction corresponding to the selected action to a device or software system. The device or software system may then execute a local version of the command or instruction.

FIGS. 4A-6B depict an exemplary imaging system 400 in various imaging orientations. The imaging system 400 includes a floor mount or base 404 for supporting the imaging system 400 on a floor. The gantry 406 extends upwards from the floor mount 404 and is rotatable to support both the tube head 408 and a support arm 410. The tube head 408 and support arm 410 are configured to rotate discretely from each other and may also be raised and lowered along a face 412 of the gantry so as to accommodate patients of different heights. An x-ray source is disposed within the tube head 408. The support arm 410 includes a support platform 414 that includes therein an x-ray receptor and other components (not shown). A compression arm 416 extends from the support arm 410 and is configured to raise and lower linearly (relative to the support arm 410) a compression paddle 418 for compression of a patient breast during imaging procedures. Together, the tube head 408 and support arm 410 may be referred to as a C-arm 409. A number of interfaces and display screens are disposed on the imaging system 400. These include a foot display screen 420, a gantry interface 422, a support arm interface 424, and a compression arm interface 426. In general the various interfaces 422, 424, and 426 may include one or more tactile buttons, knobs, switches, as well as one or more display screens, including capacitive touch screens with graphic user interfaces (GUIs) so as to enable user interaction with and control of the imaging system 400. The various interfaces 422, 424, and 426 may additionally or alternately include one or more image capture sensors and/or motion detectors (as described elsewhere herein).

Figures 4A, 4B:
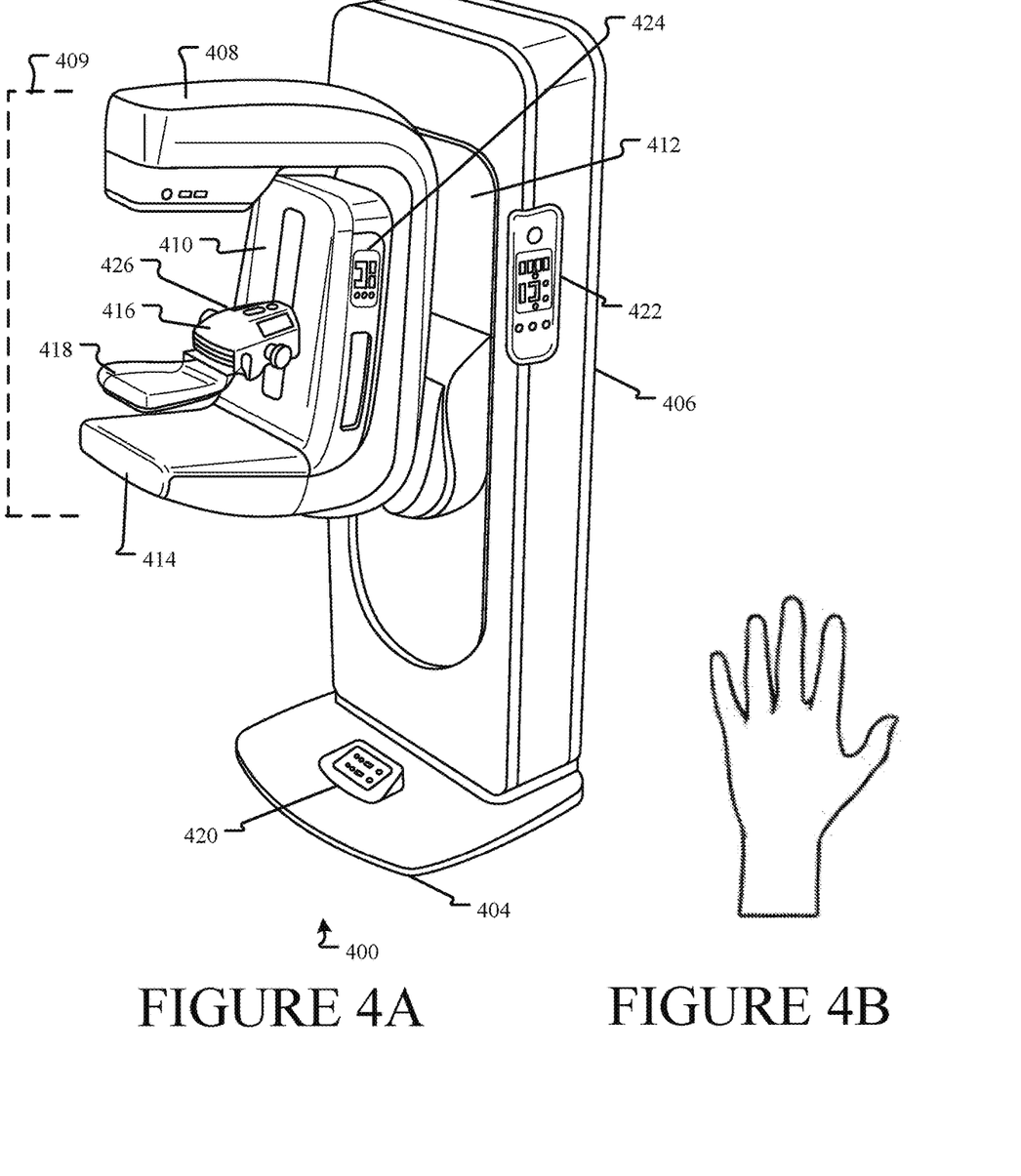
FIG. 4A depicts an imaging system in a craniocaudal (CC) imaging orientation.
FIG. 4B depicts an example hand gesture.

In aspects, imaging system 400 may implement the gesture recognition functionality described herein. As a specific example, FIG. 4A depicts imaging system 400 in a craniocaudal (CC) imaging orientation. In some examples, the CC imaging orientation may represent the default or initial orientation for imaging system 400. Accordingly, C-arm 409 may be stored in the CC imaging orientation when imaging system 400 is powered off or inactive. Alternately, C-arm 409 may be stored in alternate configuration, and may be oriented into the CC imaging orientation when imaging system 400 receives an activation signal intended to activate gesture recognition functionality. In other examples, the CC imaging orientation may correspond to one or more gestures, such as the gesture depicted in FIG. 4B (e.g., displaying an open-faced hand to imaging system 400). Although specific gestures and orientations are described herein, one skilled in the art will appreciate that other gestures and corresponding orientations are contemplated. For instance, a gesture-based system, such as American Sign Language, may be used to orient support arm 410. Further, although specific reference has been made herein to orientation of support arm 410, it will be appreciated that the movement and/or orientation of other components of imaging system 400 (and/or alternate medical devices) is contemplated. For instance, the gesture recognition techniques used to control movement of support arm 410 may also control movement of C-arm 409, compression arm 216, and/or compression paddle 218.

Figure 5A:
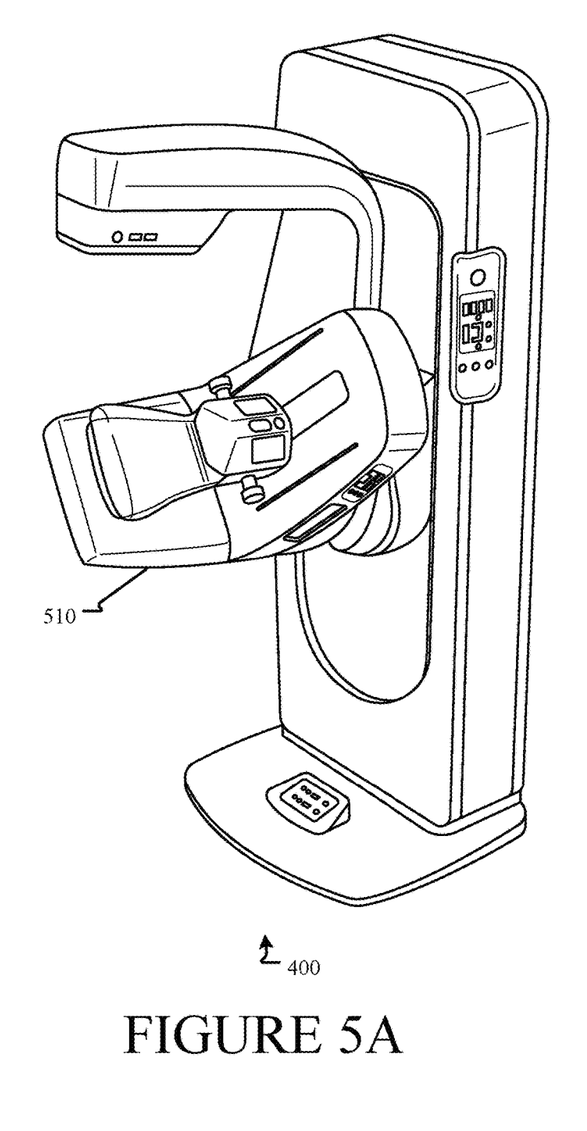
FIG. 5A depicts an imaging system in a right mediolateral oblique (RMLO) imaging orientation.
Figure 5B:
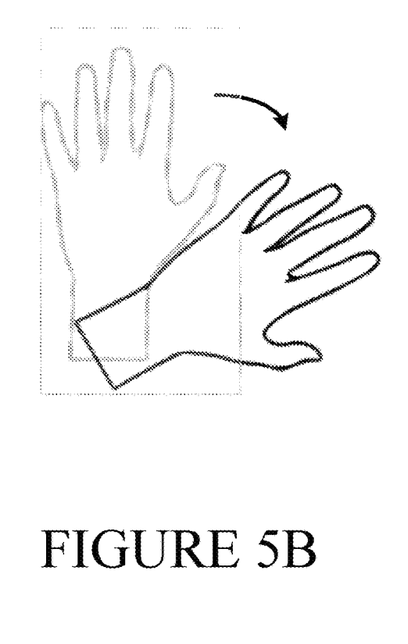
FIG. 5B depicts another example hand gesture.

FIG. 5A depicts the imaging system 400 in a breast positioning state for a right mediolateral oblique (RMLO) imaging orientation. Imaging system 400 may orient support arm 410 into the RMLO imaging orientation in response to receiving gesture input from one or more input sources, such as a healthcare professional. As one example, a radiologist interacting with imaging system 400 may perform the gesture depicted in FIG. 5B (e.g., rotating the open-faced hand depicted in FIG. 4B approximately 60 degrees clockwise). Imaging system 400 may detect the gesture using one or more of various interfaces 422, 424, and 426. As the gesture is being detected, imaging system 400 may rotate support arm 510 in real-time to approximately match the rotation in the gesture. For instance, as the open-faced hand is rotated clockwise through 15 degrees of the 60 degree arc, support arm 510 is rotated clockwise approximately 15 degrees. In another example, a radiologist interacting with imaging system 400 may perform an alternate gesture, such as displaying a first to the imaging system 400. In such an example, the image of the first may correspond to a predefined orientation of support arm 510. Upon detecting the displayed first, imaging system 400 may compare the image of the first to one or more stored images. The stored images may each be mapped to (or otherwise correspond to) an orientation of support arm 510. In response to identifying a stored image that matches the image of the first, imaging system 400 may orient support arm 510 to the orientation mapped to the matched stored image.

Figure 6A:
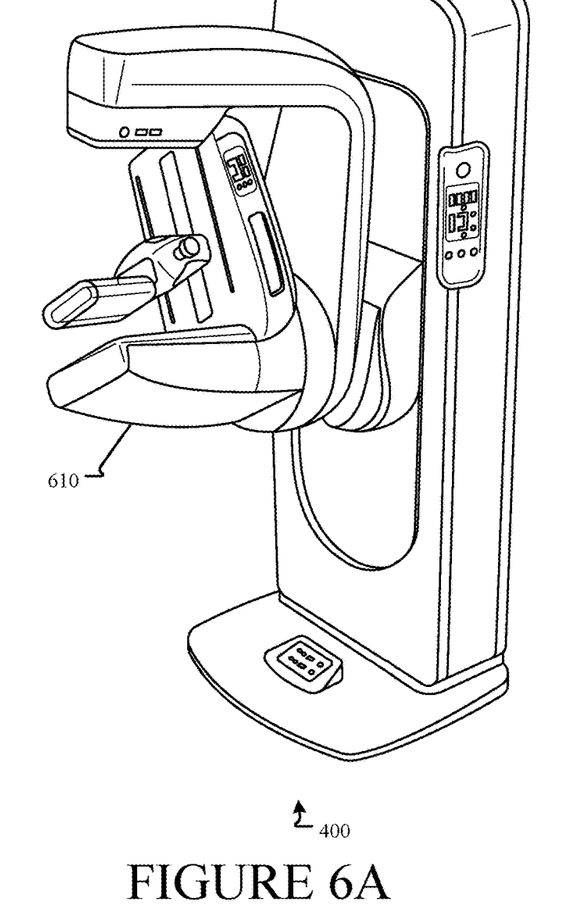
FIG. 6A depicts an imaging system in a left mediolateral oblique (LMLO) imaging orientation.
Figure 6B:
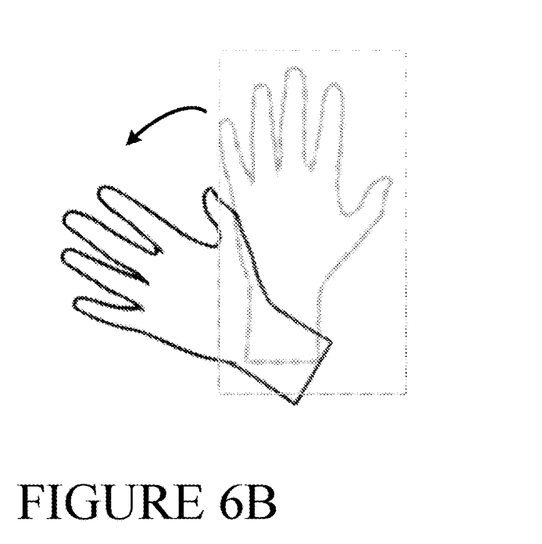
FIG. 6B depicts another example hand gesture.

FIG. 6A depicts the imaging system 400 in a breast positioning state for a left mediolateral oblique (LMLO) imaging orientation. Imaging system 400 may orient support arm 610 into the LMLO imaging orientation in response to receiving gesture input from one or more input sources. For example, a radiologist interacting with imaging system 400 may perform the gesture depicted in FIG. 6B (e.g., rotating the open-faced hand depicted in FIG. 4B approximately 60 degrees counter-clockwise). Imaging system 400 may detect the gesture and may rotate support arm 610 to approximately match the rotation in the gesture, as depicted in FIG. 5A.

Figure 7:
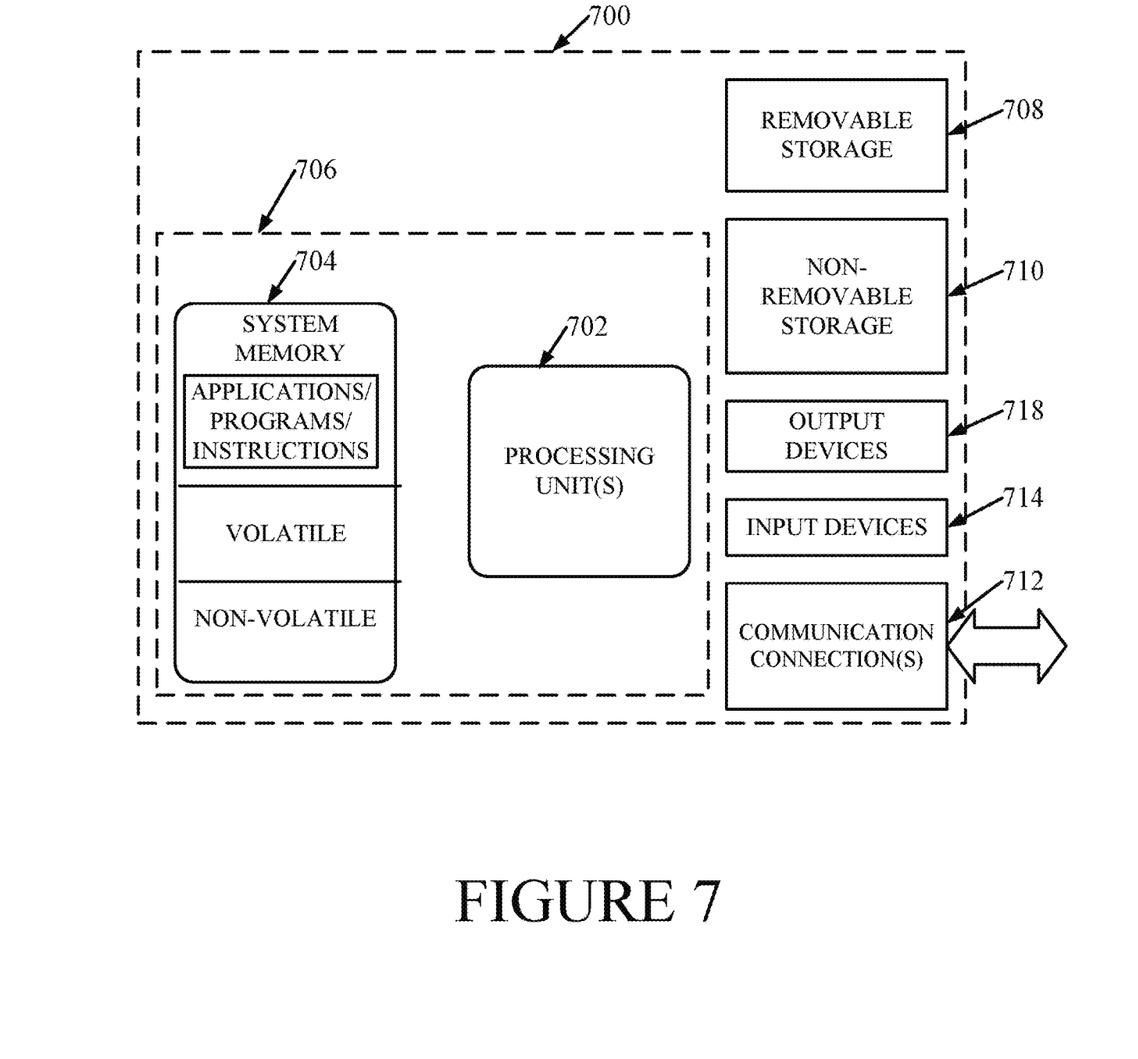
FIG. 7 illustrates one example of a suitable operating environment in which one or more of the present embodiments may be implemented.

FIG. 7 illustrates an exemplary suitable operating environment for using gesture recognition to control medical devices and software, as described in FIG. 1. In its most basic configuration, operating environment 700 typically includes at least one processing unit 702 and memory 704. Depending on the exact configuration and type of computing device, memory 704 (storing, instructions to perform the techniques disclosed herein) may be volatile (such as RAM), non-volatile (such as ROM, flash memory, etc.), or some combination of the two. This most basic configuration is illustrated in FIG. 7 by dashed line 706. Further, environment 700 may also include storage devices (removable, 708, and/or non-removable, 710) including, but not limited to, magnetic or optical disks or tape. Similarly, environment 700 may also have input device(s) 714 such as keyboard, mouse, pen, voice input, etc. and/or output device(s) 716 such as a display, speakers, printer, etc. Also included in the environment may be one or more communication connections 712, such as LAN, WAN, point to point, etc. In embodiments, the connections may be operable to facility point-to-point communications, connection-oriented communications, connectionless communications, etc.

Operating environment 700 typically includes at least some form of computer readable media. Computer readable media can be any available media that can be accessed by processing unit 702 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 700 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A system comprising:
at least one processor; and
memory coupled to the at least one processor, the memory comprising computer executable instructions that, when executed by the at least one processor, performs a method comprising:
collecting sensor data associated with gesture input, wherein the gesture input corresponds to a user interaction with a medical imaging device having a plurality of components associated therewith, and wherein each component is configured to receive a corresponding user operation that is different than the gesture input;
determining whether each of the plurality of components associated with the medical imaging device is active or inactive for the gesture input based on elapsed time between the corresponding user operation and the gesture input;
accessing one or more model templates for each active component of the medical imaging device;
processing the gesture input with respect to the one or more model templates for each active component to determine a gesture command for an active component of the medical imaging device; and
causing automated performance of the one or more actions by the active component of the medical imaging device based on the gesture command.

2. The system of claim 1, the method further comprising:
receiving an initial input;
determining the initial input is an activation signal;
based on the activation signal, activating an input detection mode; and
detecting, by the activated input detection mode, the gesture input.

3. The system of claim 2, wherein determining the initial input is an activation signal comprises comparing the initial input to a list of known wake gestures or wake words.

4. The system of claim 2, wherein the initial input is gesture input or audio input.

5. The system of claim 1, wherein the sensor data is collected using a sensor component operating in an always-on state.

6. The system of claim 1, wherein:
the plurality of components associated with the medical imaging device includes one or more hardware components and one or more software components; and
the method further comprises:
storing first model templates for the one or more hardware components, wherein different hardware components are associated with different first model templates; and
storing second model templates for the one or more software components,
wherein different software components are associated with different second model templates.

7. The system of claim 6, wherein the method further comprises:
determining a hardware component is active based on elapsed time between a detected user action of manipulating the hardware component and the gesture input; and
determining a software component is active based on elapsed time between a detected user action of manipulating the software component and the gesture input.

8. The system of claim 1, wherein processing the gesture input with respect to the one or more model templates for each active component includes comparing the gesture input and the one or more model templates for each active component with one or more gesture recognition algorithms, wherein the one or more gesture recognition algorithms comprise at least one of a 3D model-based algorithm, a skeletal-based algorithm, and an appearance-based algorithm.

9. The system of claim 8, wherein the sensor data comprises one or more images of the gesture input, and wherein the one or more gesture recognition algorithms evaluate the one or more images and the one or more model templates to determine a match which identifies at least one of a gesture, a posture, a body part, a body part orientation, or a configuration of features.

10. The system of claim 1, wherein the one or more model templates include one or more stored images, and wherein processing the gesture input includes comparing the gesture input to the one or more stored images.

11. The system of claim 1, wherein causing the automated performance of the one or more actions comprises transmitting the gesture command to the active component.

12. The system of claim 1, wherein the gesture input is provided by a user while the user is interacting with a virtualized environment.

13. The system of claim 1, wherein the one or more actions correspond to an automated physical movement of the active component.

14. The system of claim 1, wherein the one or more actions correspond to at least one of annotating an image, selecting an image, modifying the scale of content, or manipulating 3D aspects of content.

15. The system of claim 1, wherein the automated performance of the one or more actions occurs without a user making physical contact with the active component during the gesture input.

16. A method comprising:
detecting, by an input processing system, a gesture from a user, wherein the gesture is intended to manipulate one or more components associated with a medical imaging device, and wherein the user does not make physical contact with the one or more components during the gesture;
collecting, by a gesture detection sensor of the input processing system, sensor data associated with the gesture;
applying the sensor data to a gesture recognition algorithm to determine an input context for the gesture, the input context indicating whether each component of the medical imaging device is active or inactive for the gesture based on elapsed time between using each component and collecting the sensor data associated with the gesture;
based on the input context, correlating the gesture with one or more actions, wherein the one or more actions represent a manipulation of the one or more components associated with the medical imaging device; and causing, by an input processing system, the one or more components associated with the medical imaging device to automatically perform of the one or more actions.

17. The method of claim 16, wherein the input context represents a software component that was in focus when the gesture was detected.

18. The method of claim 16, wherein the input processing system provides at least one of a virtual reality environment, an augmented reality environment, and a mixed reality environment.

19. The method of claim 16, wherein correlating the gesture with one or more actions comprises applying one or more machine learning techniques to the sensor data.

20. A system comprising:
   at least one processor; and
   memory coupled to the at least one processor, the memory comprising computer executable instructions that, when executed by the at least one processor, performs a method comprising:
   receiving an input;
   determining the input is an activation signal;
   based on the activation signal, activating an input detection mode;
   detecting, by the activated input detection mode, a gesture;
   collecting sensor data associated with the gesture, wherein the gesture corresponds to a user interaction with one or more components associated with a medical imaging device;
   applying the sensor data to one or more gesture recognition algorithms to determine an input context for the gesture, the input context indicating whether each component of the medical imaging device is active or inactive for the gesture based on elapsed time between using each component and collecting the sensor data associated with the gesture;
   based on the input context, correlating the gesture with one or more actions, wherein the one or more actions represent a manipulation of the one or more components associated with the medical imaging device; and
   causing the one or more components associated with the medical imaging device to automatically perform of the one or more actions.

* * * * *